(12) United States Patent
Beale et al.

(10) Patent No.: US 10,478,235 B2
(45) Date of Patent: *Nov. 19, 2019

(54) SURGICAL TOOL

(71) Applicant: WARSAW ORTHOPEDIC, INC., Warsaw, IN (US)

(72) Inventors: Jeff Beale, Bartlett, TN (US); Harold Taylor, Memphis, TN (US); Jeffrey Chapin, Jamaica Plain, MA (US); Timothy Proulx, Nashua, NH (US); Jared Alden Judson, Medford, MA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/398,369

(22) Filed: Jan. 4, 2017

(65) Prior Publication Data

US 2017/0112550 A1 Apr. 27, 2017

Related U.S. Application Data

(60) Continuation of application No. 13/887,928, filed on May 6, 2013, now Pat. No. 9,662,160, which is a
(Continued)

(51) Int. Cl.
*A61B 17/70* (2006.01)
*B25B 21/00* (2006.01)
(Continued)

(52) U.S. Cl.
CPC ........ *A61B 17/7082* (2013.01); *B25B 21/002* (2013.01); *B25B 23/0078* (2013.01);
(Continued)

(58) Field of Classification Search
CPC ............ A61B 17/7082; B25B 23/0078; B25B 21/002

See application file for complete search history.

(56) References Cited

U.S. PATENT DOCUMENTS

| 1,343,667 A | * | 6/1920 | Evensen | ............... B25B 21/001 29/238 |
| 3,323,395 A | * | 6/1967 | Burnett | ................. B25B 21/002 173/177 |

(Continued)

OTHER PUBLICATIONS

International Search Authority, PCT US2009/038061, dated Mar. 24, 2009.

*Primary Examiner* — Christian Sevilla

(57) ABSTRACT

A surgical tool for removing a portion of an implant is provided that includes a housing, a motor contained within the housing and coupled to the housing, and an output shaft having a distal end and a proximal end opposite the distal end, wherein the proximal end is coupled to the motor and the distal end has an opening configured to rotatably engage an implant. The surgical tool further includes a counter-torque sleeve extending around the output shaft having a proximal end and a distal end opposite the proximal end, wherein the proximal end is coupled to the housing and the distal end is configured to couple to the implant relative to the counter-torque sleeve. Upon a rotational force to the implant, the forces transmitted by the output shaft and the counter-torque sleeve are balanced by the coupling of the output shaft and counter-torque sleeve through the housing.

20 Claims, 17 Drawing Sheets

Related U.S. Application Data division of application No. 12/104,623, filed on Apr. 17, 2008, now Pat. No. 9,017,333.

(51) Int. Cl.
    *B25B 23/00*     (2006.01)
    *B25B 23/14*     (2006.01)
    *B25B 23/147*     (2006.01)
    *H01M 2/10*     (2006.01)
    *A61B 17/00*     (2006.01)
    *A61B 90/00*     (2016.01)

(52) U.S. Cl.
    CPC ........ *B25B 23/0085* (2013.01); *B25B 23/141* (2013.01); *B25B 23/147* (2013.01); *H01M 2/105* (2013.01); *A61B 2017/00398* (2013.01); *A61B 2017/00477* (2013.01); *A61B 2017/00734* (2013.01); *A61B 2090/031* (2016.02); *H01M 2220/30* (2013.01)

(56) References Cited

U.S. PATENT DOCUMENTS

| | | | | |
|---|---|---|---|---|
| 3,331,269 A * | 7/1967 | Sauter | ................... | B25B 21/002 81/56 |
| 4,289,049 A * | 9/1981 | Rebish | ................. | B25B 21/002 81/56 |
| 4,862,773 A * | 9/1989 | Batten | ..................... | B25B 13/48 81/13 |
| 6,062,575 A | 5/2000 | Mickel et al. | | |
| 2002/0058958 A1* | 5/2002 | Walen | ................ | A61B 17/1615 606/170 |
| 2004/0143265 A1 | 7/2004 | Landry et al. | | |

\* cited by examiner

US 10,478,235 B2

SURGICAL TOOL

CROSS-REFERENCE TO RELATED APPLICATIONS

This application is a continuation application of U.S. patent application Ser. No. 13/887,928, filed on May 6, 2013, which is a divisional application of U.S. patent application Ser. No. 12/104,623, filed on Apr. 17, 2008, now U.S. Pat. No. 9,017,333. These applications are incorporated herein by reference herein, in their entireties.

BACKGROUND

Field of the Disclosure

This disclosure is directed to a surgical tool, and more particularly directed toward a surgical tool for removing a portion of an implant.

Description of the Related Art

There are a variety of different spinal diseases, such as scoliosis, as well as others, which may be cured or mitigated by implantation of certain devices. Such devices can include articles and mechanisms useful for repairing damaged portions of the spine, stabilizing portions of the spine, or changing the position of the spine to a more healthy state. For example, rod and anchor systems are commonly employed when portions of the spine need to be realigned, such as in patients with abnormal curvatures, wherein the rod provides rigid support for urging the spine to a more healthy position.

Typically, the process of implanting rod and anchor systems can be quite daunting, including the implantation of multiple anchors or bone screws within particular locations of the spine and then attaching each of the anchors to a rod. Depending upon the severity of the spinal disease and the necessary suitable treatment, such surgeries can last hours if not more. Moreover, most of the components used in the surgery are rigid components that must be physically manipulated by a surgeon while in the patient (i.e., in-situ) leading to potential physical harm to the patient as some of the procedures can result in substantial jarring of the patient including for example, shearing off the head portions of set screws for permanent placement. Additionally, such manipulation by a surgeon may also compromise the integrity of the implanted object lessening its capabilities. Given the delicacy of surgical procedures and the anatomical importance of the spine, jarring of the patient during such surgical procedures is inherently dangerous. Additionally, the vast majority of these surgical procedures are completed by handheld manual tools, meaning hours of rigorous work for a surgeon to implant all the screws and properly align the spine with an implanted rod.

SUMMARY

DETAILED DESCRIPTION

Description of Relevant Anatomy

Figure 1:
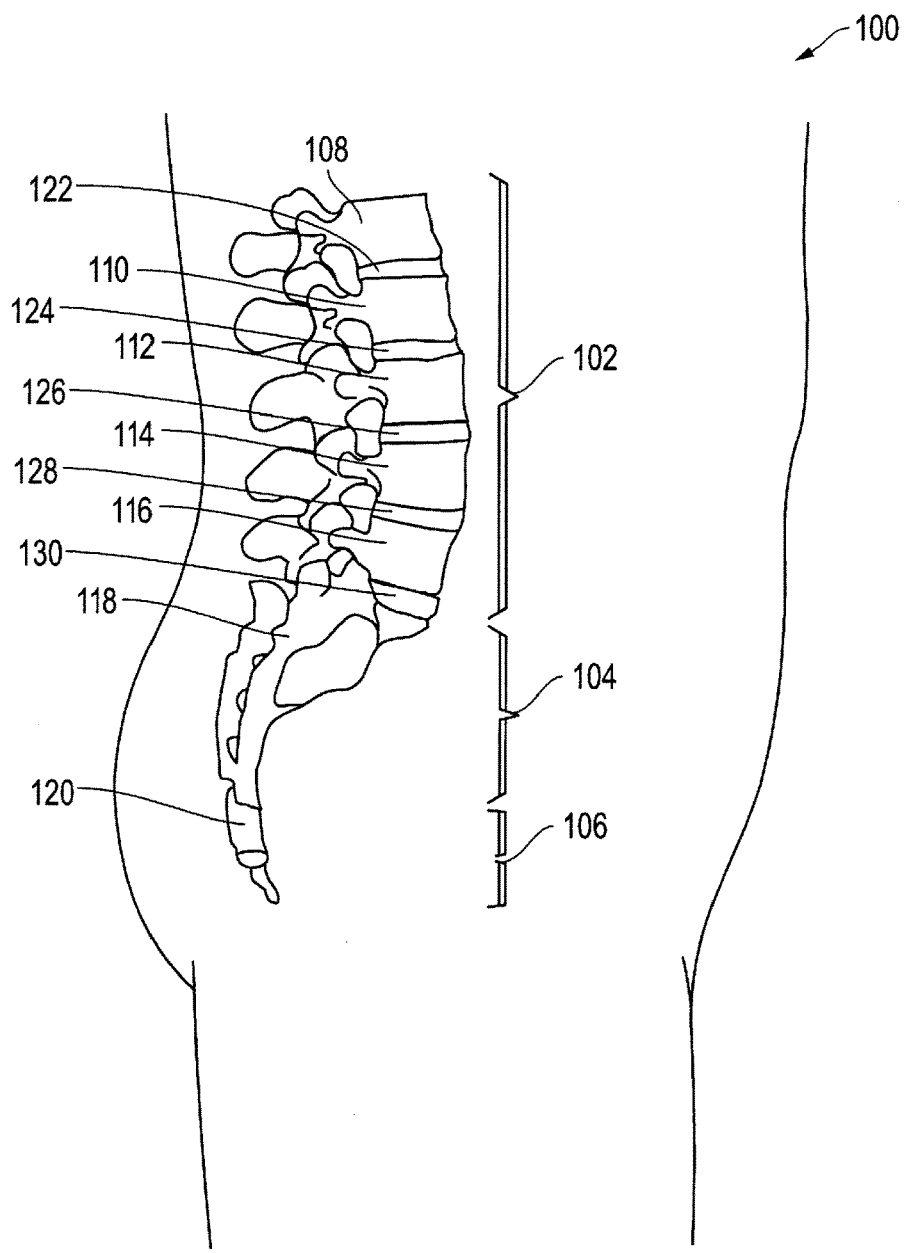
FIG. 1 includes a lateral view of a portion of a vertebral column.

Referring initially to FIG. 1, a portion of a vertebral column, designated 100, is shown. As depicted, the vertebral column 100 includes a lumbar region 102, a sacral region 104, and a coccygeal region 106. The vertebral column 100 also includes a cervical region and a thoracic region. For clarity and ease of discussion, the cervical region and the thoracic region are not illustrated.

As illustrated in FIG. 1, the lumbar region 102 includes a first lumbar vertebra 108, a second lumbar vertebra 110, a third lumbar vertebra 112, a fourth lumbar vertebra 114, and a fifth lumbar vertebra 116. The sacral region 104 includes a sacrum 118. Further, the coccygeal region 106 includes a coccyx 120.

As depicted in FIG. 1, a first intervertebral lumbar disc 122 is disposed between the first lumbar vertebra 108 and the second lumbar vertebra 110. A second intervertebral lumbar disc 124 is disposed between the second lumbar vertebra 110 and the third lumbar vertebra 112. A third intervertebral lumbar disc 126 is disposed between the third lumbar vertebra 112 and the fourth lumbar vertebra 114. Further, a fourth intervertebral lumbar disc 128 is disposed between the fourth lumbar vertebra 114 and the fifth lumbar vertebra 116. Additionally, a fifth intervertebral lumbar disc 130 is disposed between the fifth lumbar vertebra 116 and the sacrum 118.

In a particular embodiment, if one of the intervertebral lumbar discs 122, 124, 126, 128, 130 is diseased, degenerated, or damaged or if one of the zygapophyseal joints is diseased, degenerated or damaged, that disc or joint can be treated with an implanted device.

Figure 2:
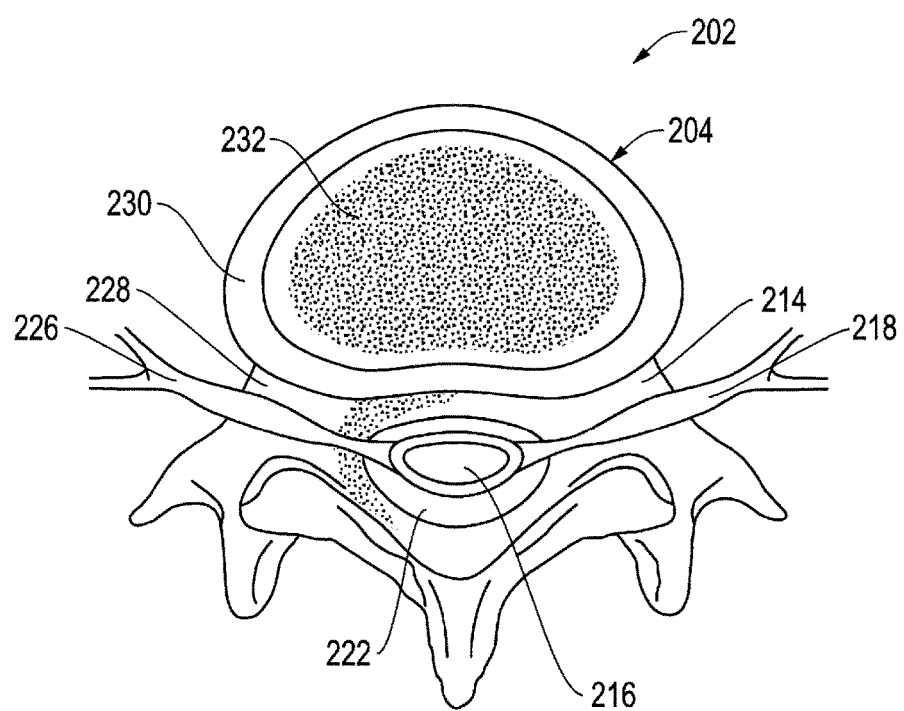
FIG. 2 includes a top plan view of a vertebra.

Referring to FIG. 2, a top plan view of a vertebra is illustrated. As shown, the vertebral body 204 of the inferior vertebra 202 includes a cortical rim 230 composed of cortical bone. Also, the vertebral body 204 includes cancellous bone 232 within the cortical rim 230. The cortical rim 230 is often referred to as the apophyseal rim or apophyseal ring. Further, the cancellous bone 232 is generally softer than the cortical bone of the cortical rim 230.

As illustrated in FIG. 2, the inferior vertebra 202 further includes a first pedicle 214, a second pedicle 228, a first lamina 220, and a second lamina 224. Further, a vertebral foramen 222 is established within the inferior vertebra 202. A spinal cord 216 passes through the vertebral foramen 222. Moreover, a first nerve root 218 and a second nerve root 226 extend from the spinal cord 216. In particular, the first pedicle 214 and the second pedicle 228 represent regions of the spine in which surgeons often choose to implant anchors, such as bone screws for attaching an anchor and rod system to the spine. Notably, given the proximity to the spinal cord 216 and other significant anatomical portions, the implantation of such screws is a delicate and precise procedure requiring tools significantly different than available to the general public.

The vertebrae that make up the vertebral column have slightly different appearances as they range from the cervical region to the lumbar region of the vertebral column. However, all of the vertebrae, except the first and second cervical vertebrae, have the same basic structures, e.g., those structures described above in conjunction with FIG. 2. The first and second cervical vertebrae are structurally different than the rest of the vertebrae in order to support a skull.

Figure 3:
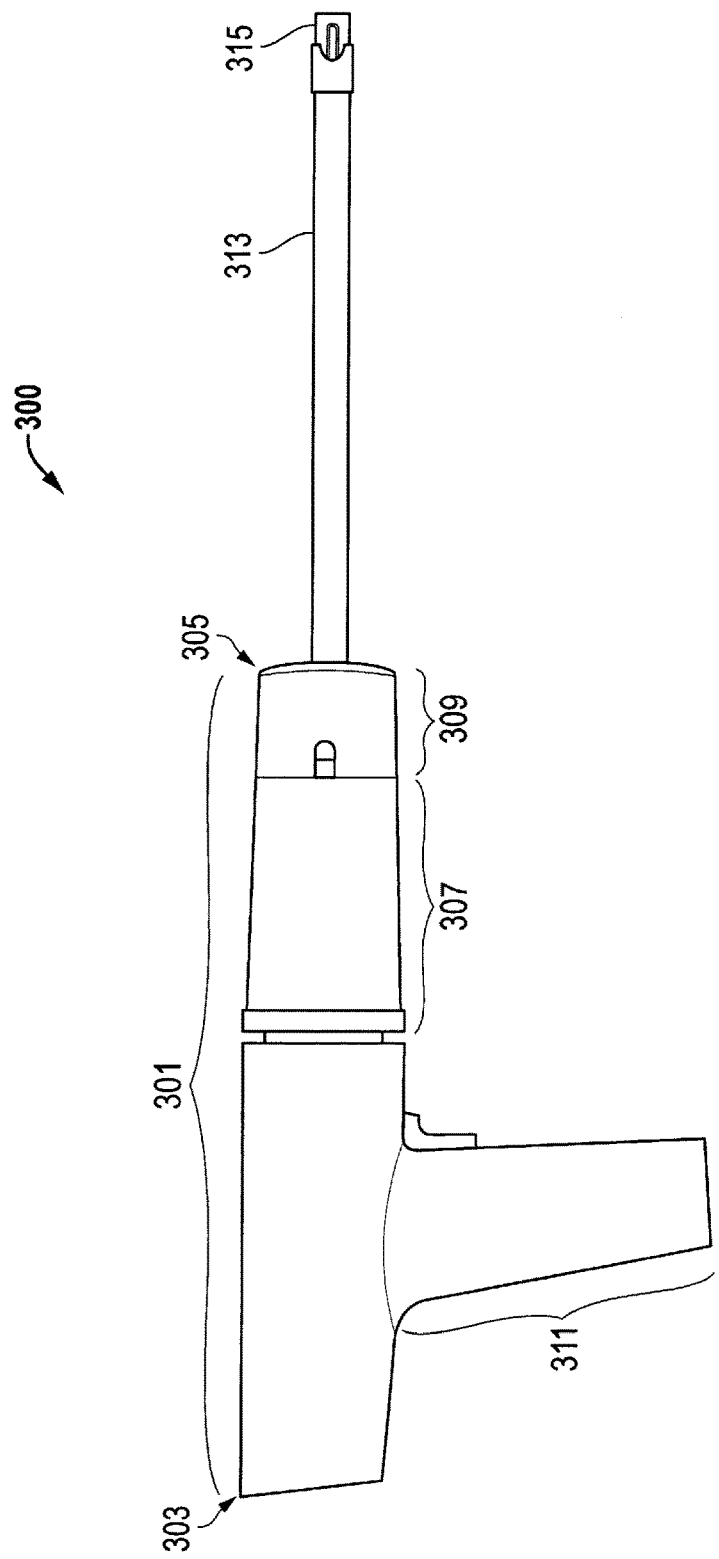
FIG. 3 includes a side view of a surgical tool in accordance with an embodiment.

Referring now to FIGS. 3-19 embodiments describing a surgical tool, its components and methods of using the surgical tool are provided. Accordingly, referring to FIG. 3 a side view illustration of a surgical tool is provided in accordance with an embodiment. As illustrated, a surgical tool 300 includes a housing 301 having a proximal end 303 and a distal end 305. The housing 301 further includes a handle portion 311 coupled to the housing 301 between the proximal end 303 and the distal end 305. As further illustrate, the surgical tool 300 includes a bayonet portion 309 coupled to the housing 301 adjacent to the distal end 305, and a sleeve portion 307 coupled to the housing 301 and abutting the bayonet portion 309. The surgical tool 300 further includes an effector, or in particular embodiments, an output shaft 315, coupled to the housing 301 adjacent to the distal end 305. The surgical tool 300 further includes a reaction arm, or in accordance with particular embodiments, a counter-torque sleeve 313, overlying the output shaft 315 and coupled to the housing 301 adjacent to the distal end 305.

Figure 4:
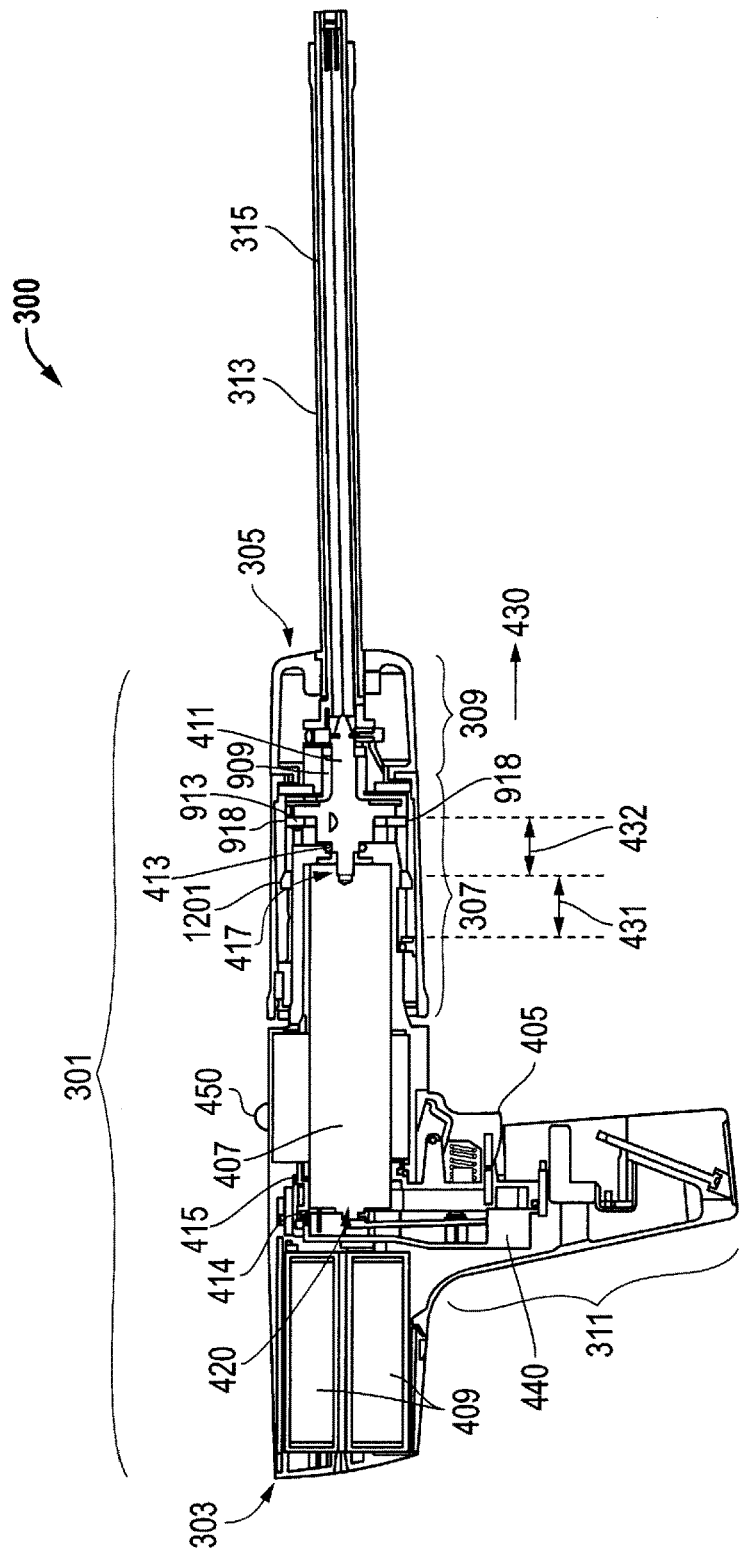
FIG. 4 includes a cross-sectional illustration of a surgical tool in accordance with an embodiment.

Referring to the surgical tool 300 with more particularity, FIG. 4 provides a cross-sectional illustration of the surgical tool in accordance with one embodiment. The cross-sectional illustration of FIG. 4 is provided for clarity and to illustrate the interaction of all the components, as such may be referred to throughout the detailed description.

In reference to the operation of the tool, generally the surgical tool 300 is capable of providing a rotational force to an implant via the output shaft 315. In particular, a user depresses a trigger 405 coupled to the handle 311 which is coupled to an actuator 440. The actuator 440 is coupled to a motor 407 and configured to engage the motor 407 such that a motor shaft 411 is rotated upon actuation of the motor 407. Depending upon the position of a sleeve portion 307 and components within the sleeve portion, which will be described in more detail herein, the motor shaft 411 can be coupled to the output shaft 315 which in turn will cause rotation of the output shaft 315. According to a particular embodiment, coupling of the motor shaft 411 and output shaft 315 is facilitated by axial movement of the sleeve portion 307 such that components within the sleeve including a spline drive 913 and hex drive output gear 909 are operably coupled and result in coupling of the motor shaft 411 and the output shaft 315. Moreover, axial movement of the sleeve portion 307 causes respective axial movement of the counter-torque sleeve 313 such that the counter-torque sleeve 313 can be positioned on the implant engaged by the output shaft 315.

In further reference to the general operation of the surgical tool 300, the motor 407 can be a DC electric motor and accordingly can be electrically connected to power sources 409, including for example batteries. According to one embodiment, the power sources 409 can be disposed in a housing, such as a battery pack, that is adjacent to the proximal end 303 of the housing 301.

The surgical tool 300 can further include optical indicator 450 coupled to the housing and configured to provide feedback to the user regarding a state of the tool. Generally, the optical indicator 450 can be electrically coupled to the power sources 409. In one embodiment, the optical indicator 450 can include a light, such as a light emitting diode (LED). In a more particular embodiment, the optical indicator 450 can indicate whether the sleeve portion 307 and the counter-torque sleeve 313 have traveled a requisite axial distance such that the tool will operate. Accordingly, in such embodiments, the light may further be electrically coupled to a switch or a microprocessor.

Additionally, the surgical tool 300 can further include an audible indicator coupled to the housing and configured to provide feedback to the user regarding a state of the tool. Accordingly, the audible indicator can provide the same function as the optical indicator as described above.

In reference to components at the distal end of the surgical tool 300, according to one embodiment, the output shaft 315 is coupled to the housing 301. According to a particular embodiment, the output shaft 315 is coupled to the motor shaft 411 which is directly connected to the motor 407 and the motor is directly connected to the housing 301. Moreover, the counter-torque sleeve 313 overlies the output shaft 315 and is coupled to the housing 301. In accordance with one particular embodiment, the counter-torque sleeve 313 is directly connected to the bayonet 309 that is a portion of the housing 301. As such, in accordance with an aspect of the present disclosure, the output shaft 315 and the counter-torque sleeve 313 are coupled to the housing such that upon rotation of the output shaft 315 on an implant the forces transmitted by the output shaft 315 and the counter-torque 313 are balanced by their respective couplings to the housing 301.

As the surgical tool 300 is intended for use in operatories, the tool, and more particularly components contained therein, must be sterilizable. As such, in accordance with one particular embodiment, components of the surgical tool 300, including for example, the output shaft 315, the counter-torque sleeve 313, the bayonet portion 309, and portions of the housing 301 are made of materials that are autoclavable. As such, the components must be capable of withstanding temperatures in excess of 130° C., as well as pressures in excess of 140 psi. In one embodiment, components illustrated in FIG. 3 can be made of a metal or metal alloy. Suitable metal or metal alloys can include tungsten, magnesium, aluminum, iron, cobalt, nickel, titanium, steel, chromium, or any combinations thereof. In another embodiment, the components illustrated in FIG. 3 can include a non-metal, such as carbon, and more particularly carbon fiber. In accordance with another embodiment, the components within the surgical tool 300 can include high temperature polymer materials. In a more particular embodiment, suitable polymer materials can include polyurethane materials, polyolefin materials, polyether materials, silicone materials, or a combination thereof. Further, the polyolefin materials can include polypropylene, polyethylene, halogenated polyolefin, fluoropolyolefin, or a combination thereof. The polyether materials can include polyetherketone (PEK), polyetheretherketone (PEEK), polyetherketoneketone (PEKK), polyaryletherketone (PAEK), or a combination thereof. Other suitable materials can include styrenes (e.g., acrylonitrile butadiene styrene), polycarbonates, and polysulphones.

Moreover, portions of the housing 301 can be sealed. In accordance with one particular embodiment, the motor 407 is within the sealed portion of the housing 301. In accordance with another embodiment, seals 413, 414, and 415, such as o-rings, which are provided to create a sealed portion around the motor 407 such that the surgical tool 300 can be sterilized without damaging the motor 407. In a more particular embodiment, a single o-ring 413 is provided between the distal end 417 of the motor 407 and the motor shaft 411, while a double o-ring seal provided by o-rings 414 and 415 are provided proximate to the proximal end 420 of the motor 407.

According to one particular embodiment, the torque provided by the output shaft to an implant can be limited, and more particularly selectable. According to one embodiment, the torque output by the tool can be limited by an electrical system wherein the current provided to the motor is controlled and may be selectable by the user. In such an embodiment, a microprocessor can be electrically coupled to the motor and battery to control the current to the motor. According to an alternative embodiment, a mechanical torque limiter can be coupled to the motor shaft to limit the torque. In one such embodiment, the torque limiter can include the use of bearings and a clutch which disengages an input shaft from an output shaft if a certain torque is exceeded.

Figure 5:
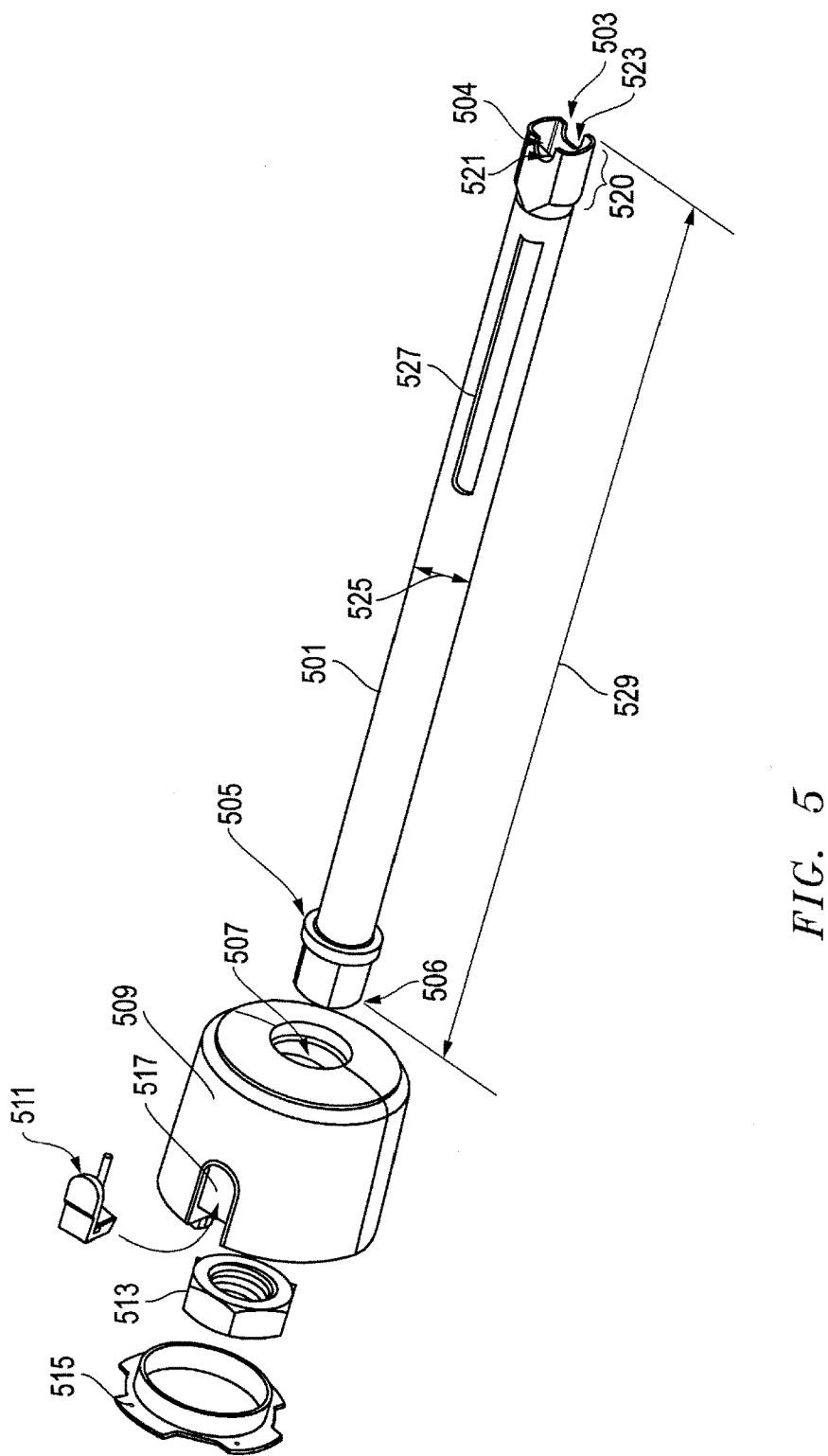
FIG. 5 includes a perspective view of the bayonet portion of the surgical tool in accordance with an embodiment.

Referring now to particular portions of the surgical tool 300, FIG. 5 includes a perspective view of a portion of the surgical tool including the counter-torque sleeve and the bayonet portion in accordance with an embodiment. Generally, the counter-torque sleeve 501 includes a proximal end 506 and a distal end 504. Moreover, the counter-torque sleeve 501 includes an opening 503 adjacent to the distal end 504 and configured to engage a portion of an implant. The counter-torque sleeve 501 can be coupled, more particularly directly connected to the bayonet portion 509 through the opening 507. In accordance with a particular embodiment, the counter-torque sleeve 501 is directly connected to the bayonet portion 509 such that the ring portion 505 adjacent to the proximal end 506 of the counter-torque sleeve 501 engages the inner surface of the bayonet portion 509 and fixably attaches the two components. Additionally, a nut 513 having threads along the inner surface can be coupled to the distal end 506 of the counter-torque sleeve 501 and directly connect the counter-torque sleeve 501 with the bayonet portion 509. Moreover, a lock ring 515 can be inserted within the bayonet portion 509 to facilitate coupling of the bayonet 509 and counter-torque sleeve 501 with the housing of the tool.

In accordance with one embodiment, the bayonet portion 509 can further include a decoupling structure to release the bayonet portion 509 from the housing of the tool. In one particular embodiment, the bayonet portion 509 includes a release tab 511 directly connected to the bayonet portion 509 and configured to be depressed and facilitate removal of the bayonet portion 509 from the housing.

As illustrated, the counter-torque sleeve 501 includes the opening 503 adjacent to the distal end 504 and configured to engage an implant. In accordance with one embodiment, the counter-torque sleeve 501 includes a head portion 520 shaped to include channels 521 and 523 that are configured to engage an implant. In a particular embodiment, the channels 521 and 523 are particularly designed to engage an implanted rod. In an alternative embodiment, the counter-torque sleeve 501 can include a pin extending from the head portion 520 configured to engage the implant and lock the position of the counter-torque sleeve 501 relative to the implant. In another particular embodiment, the head portion 520 can include more than one pin, such as two pins, that may be oriented on opposite sides of the head portion 520 and configured to engage the implant. Still, in accordance with another embodiment, the head portion 520 can be a conformable construct. For example, a conformable construction can include an array of pins disposed within the head portion 520, such that each of the pins are axially movable along the length of the counter-torque sleeve 501 and upon engagement with an implant, some of the pins are moved axially, while others are remain unmoved and couple with the engagement.

Generally, the counter-torque sleeve 501 can be freely rotatable around the longitudinal axis defined by the length. Rotational freedom facilitates initial engagement of the head portion 520 with an implant. In one embodiment, the counter-torque sleeve 501 is freely rotatable around the longitudinal axis by an angle of at least about 20°. In accordance with another embodiment, the angle of rotation can be greater, such as at least about 30°, at least about 45°, or even at least about 60°. In one particular embodiment, the counter-torque sleeve 501 is freely rotatable around the longitudinal axis by an angle of not greater than about 360°, not greater than about 180°, or even not greater than about 90° to facilitate engagement with the implant.

Generally, the counter-torque sleeve 501 has a length 519 defined between the proximal end 506 and the distal end 504 of at least about 15 cm. In accordance with another embodiment, the length 519 of the counter-torque sleeve 501 can be greater, such as at least about 18 cm, such as at least about 20 cm, or even at least about 22 cm. Still, however, in accordance with another embodiment, the length 519 of the counter-torque sleeve 501 is generally not greater than about 40 cm, such as not greater than about 30 cm, or even not greater than about 25 cm. In accordance with one particular embodiment, the counter-torque sleeve 501 has a length 519 within a range between about 20 cm and about 25 cm.

Additionally, the counter-torque sleeve 501 typically has a diameter 525 along its mid-length that is greater than a diameter of the output shaft such that the output shaft can extend through the interior of the counter-torque sleeve 501 and the counter-torque sleeve 501 can slidably engage the output shaft and portions of the implant. As such, in one particular embodiment, the counter-torque sleeve 501 has a diameter 525 of at least about 8 mm. In another embodiment, the diameter 525 is greater, such as at least about 9 mm, or even at least about 10 mm. In accordance with one particular embodiment, the diameter 525 of the counter-torque sleeve 501 is not greater than about 15 mm, such as not greater than about 12 mm. As such, in one more particular embodiment, the diameter 525 of the counter-torque sleeve 501 is within a range between about 10 mm and about 12 mm.

Still, it should be noted that while the illustrated embodiments describe the arrangement of the output shaft within the counter-torque sleeve 501, in certain alternative embodiments, the counter-torque sleeve 501 is located within the output shaft. In such embodiments the output shaft is external to the counter-torque sleeve 501, and the counter-torque sleeve 501 is disposed within the interior of the output shaft, and configured to engage portion of the implant. For example, in one particular embodiment, the implant can include a nut with a screw extending through it, wherein the counter-torque sleeve 501 is configured to engage the head of the screw, while the output shaft has a greater diameter, slideably engages over the counter-torque sleeve 501 and is configured to engage the nut. Accordingly, for such embodiments, the diameter of the counter-torque sleeve 501 can be less than described above.

In another embodiment, the counter-torque sleeve 501 can include a viewing port 527 along its length 519. In particular, the viewing port 527 can include an opening or transparent portion whereby the user can view the underlying output shaft contained within the interior of the counter-torque sleeve 501. More particularly, the viewing port 527 can be aligned with a similar structure (i.e., another viewing port) within the output shaft thereby allowing the user to view contents within the output shaft. In accordance with one particular embodiment, the tool can be used to sever break-off portions of set screws and, accordingly, the viewing port 527 allows the user to confirm separation of the break-off portion as well as identify the number of break-off portions contained within the output shaft.

Generally, the viewing port extends for a portion of the length of the counter-torque sleeve 501. In one embodiment, the viewing port extends for a length of at least about 10% of the total length 519 of the counter-torque sleeve. In another embodiment, the viewing port extends for a length of at least about 25%, such as at least about 50%, or at least 75% of the total length 519 of the counter-torque sleeve 501. In one particular embodiment, the viewing port 527 can extend for substantially the entire length 519 of the counter-torque sleeve 501.

Additionally, the viewing port 527, or alternatively a portion of the counter-torque sleeve 501 can include indicia suitable for counting the number of contents therein. In the particular context of head portions removed from set screws, assuming all of the head portions have an equal length, indicia can be provided along the length of the viewing port 527 or along the length of the counter-torque sleeve 501 that facilitate counting of the head portions contained within.

As will be described in later embodiments, the counter-torque sleeve 501 is capable of axially translating along the length 519. In particular, some axial translation of the counter-torque sleeve 501 is required for operation of the tool. The particulars of this configuration and operation will be described in later embodiments.

Figure 6:
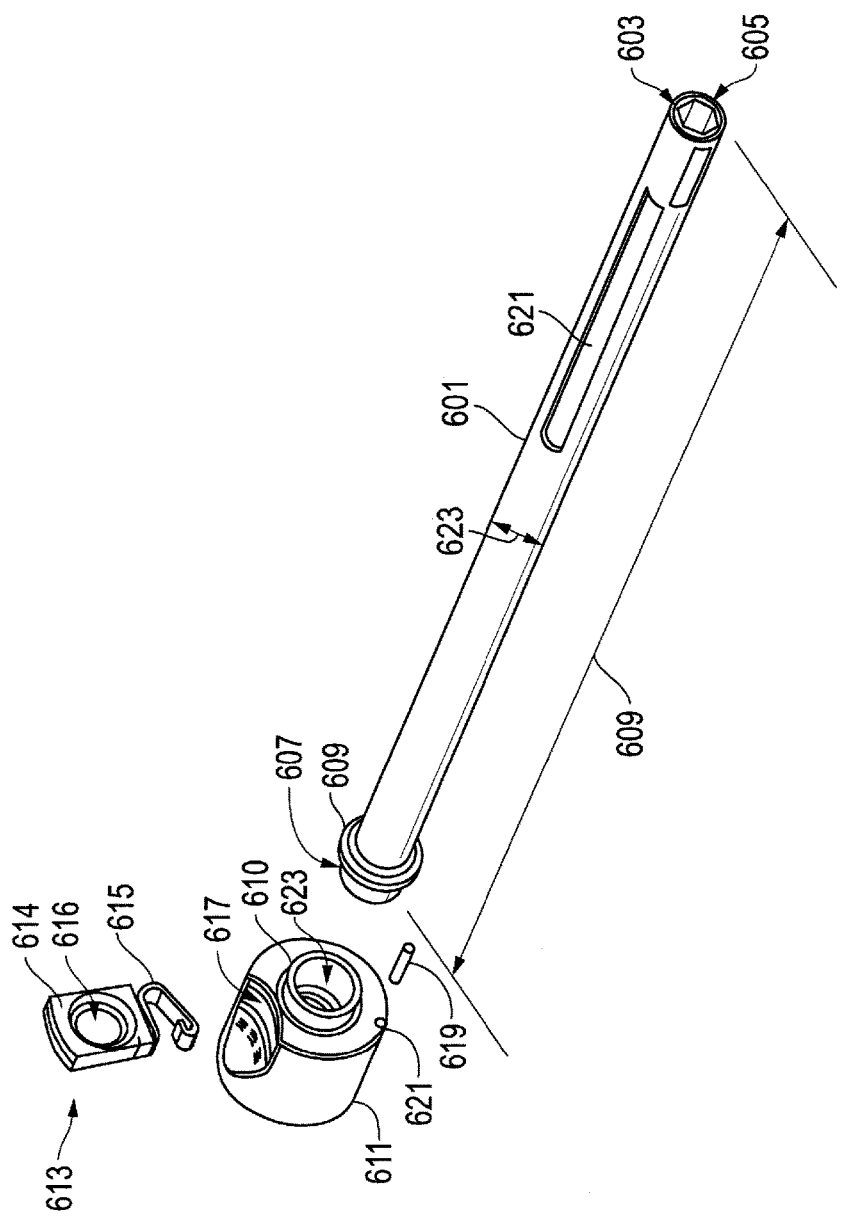
FIG. 6 includes a perspective view of a portion of the output shaft of the surgical tool in accordance with an embodiment.

FIG. 6 includes a perspective view of portions of the output shaft and inner coupler of the tool in accordance with an embodiment. As illustrated, FIG. 6 includes an output shaft 601, an inner coupling portion 611, and a coupler 613. As illustrated, the portion of the output shaft 601 adjacent to the proximal end 607 can slidably engage the interior surface of the collar 610 of the inner coupling portion 611. In particular, the inner coupling portion 611 includes an opening 617 for receiving the coupling device 613. In particular, the coupling device 613 includes an upper portion 614 having an opening 616 and a biasing member 615 connected thereto. In accordance with a particular embodiment, the opening 616 is configured to engage the end of the motor shaft as will be illustrated in further embodiments. Moreover, a pin 619 is configured to be received within an opening 621 and engage the biasing member 615 of the coupling device 613 thereby operably connecting the coupler 613 and the inner coupling portion 611.

In particular reference to the output shaft 601, the output shaft 601 includes a proximal end 607 and a distal end 603 opposite the proximal end 607. Moreover, the output shaft 601 includes an opening 605 configured to engage an implant. In accordance with a particular embodiment, the opening 605 is configured to engage a head portion of a set screw, wherein the head portion is intended to be broken off or sheared from the bottom portion of the bone screw.

Generally, the output shaft 601 has a length 609 that is particularly designed to facilitate surgical procedures, notably a length suitable to minimize tool entrance into the body and avoid contamination of the surgical site while still having a suitable length for providing significant tactile feedback required for performing skilled surgical procedures. As such, in accordance with one embodiment, the output shaft 601 has a length of at least about 10 cm. In one embodiment, the output shaft 601 has a length 609 of at least about 15 cm, such as at least about 18 cm, or even at least about 20 cm. In another embodiment, the length 609 of the output shaft 601 is not greater than about 40 cm. Still, the length 609 of the output shaft 601 may be further limited, such as not greater than about 35 cm, or not greater than about 30 cm. As such, in one particular embodiment, the output shaft 601 has a length 609 within a range between about 20 cm and about 30 cm. The output shaft 601 further includes a viewing port 621 having the same characteristics as the viewing port described in accordance with FIG. 5.

Generally, the output shaft 601 has a diameter 623 measured along the mid-region between the proximal end 607 and the distal end 603 that is less than the diameter of the counter-torque sleeve. In one embodiment, the output shaft 601 has a diameter 623 of at least about 3 mm. In another embodiment, the diameter 623 is greater, such as at least about 4 mm, at least about 5 mm, or even at least about 6 mm. Typically, however, the diameter 623 of the output shaft 601 is limited such that it is not greater than about 12 mm. As such, in one particular embodiment, the output shaft 601 has a diameter 623 within a range between about 6 mm and about 10 mm.

As previously described, in some embodiments, the output shaft 601 can have a diameter that is greater than the diameter of the counter-torque sleeve, because in such embodiments the counter-torque sleeve is configured to be disposed within the output shaft 601. As such, in these embodiments, the diameter of the output shaft can be greater, such as greater than about 10 mm, greater than about 20 mm, or even greater than about 30 mm. Generally, in accordance with such embodiments, the diameter of the output shaft is within a range between about 10 mm and about 40 mm, and more particularly within a range between 10 mm and about 30 mm.

Figure 7:
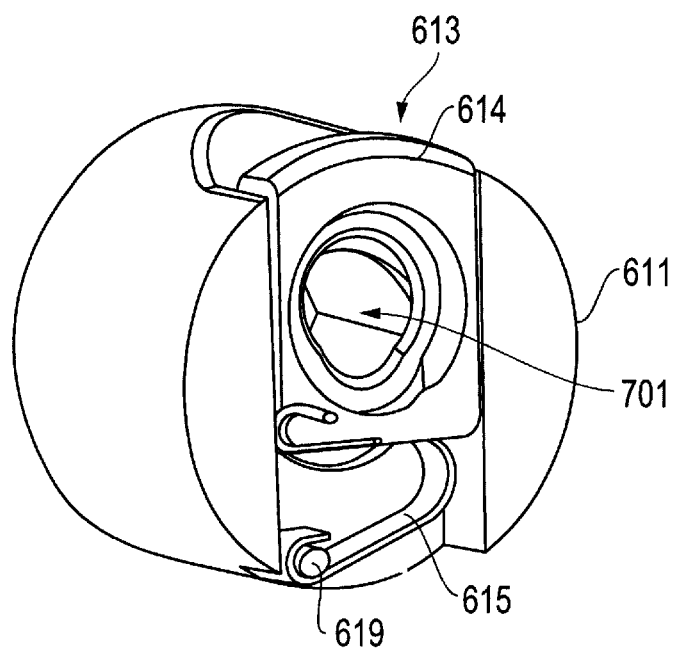
FIG. 7 includes a partial cross-section of a portion of the output shaft of the surgical tool in accordance with an embodiment.

Referring to FIG. 7, a partial cross-sectional illustration of the inner coupling portion 611 is illustrated for further clarity in accordance with an embodiment. As illustrated, the coupling device 613 is engaged within a slotted opening of the inner coupling portion 611. Generally, the pin 619 is configured to engage the biasing member 615 such that the coupler 613 is held within the coupling portion 611 until the user presses and releases the pin 619 from the biasing member. The coupler 613, and more particularly the opening 701, is designed to be of a size to prevent captured portions of an implant from falling into the tool during use or into the surgical field when the output shaft 601 is removed from the tool.

Figure 8:
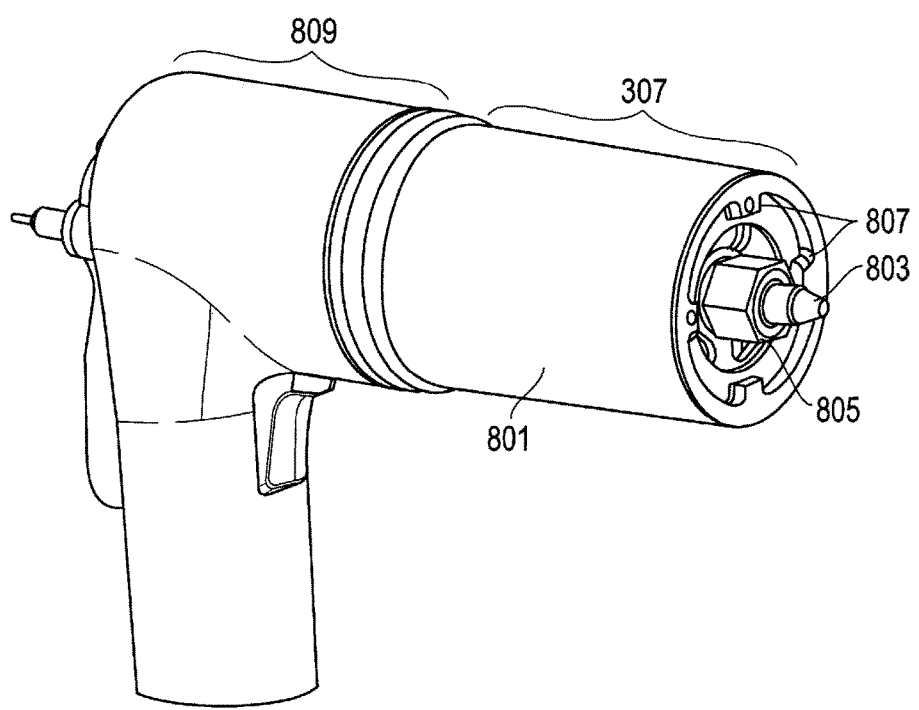
FIG. 8 includes a perspective view of a portion of the housing and sleeve of the surgical tool in accordance with an embodiment.

FIG. 8 includes a perspective view of a portion of the surgical tool in accordance with an embodiment. FIG. 8 illustrates a portion of the housing 809 and more particularly the sleeve portion 307 previously illustrated in FIG. 3. The sleeve portion 307 includes an outer sleeve 801, which further includes flanges 807 configured to engaged the lock ring 515 of the bayonet portion 509 previously illustrated in FIG. 5. Moreover, FIG. 8 further illustrates a distal end of the motor shaft 803 extending from the sleeve portion 307. In accordance with one embodiment, it is this distal end of the motor shaft 803 which is configured to engage the opening 701 within the coupling device 613 and thus the inner coupling portion 611 previously illustrated in FIGS. 6 and 7.

Figure 9:
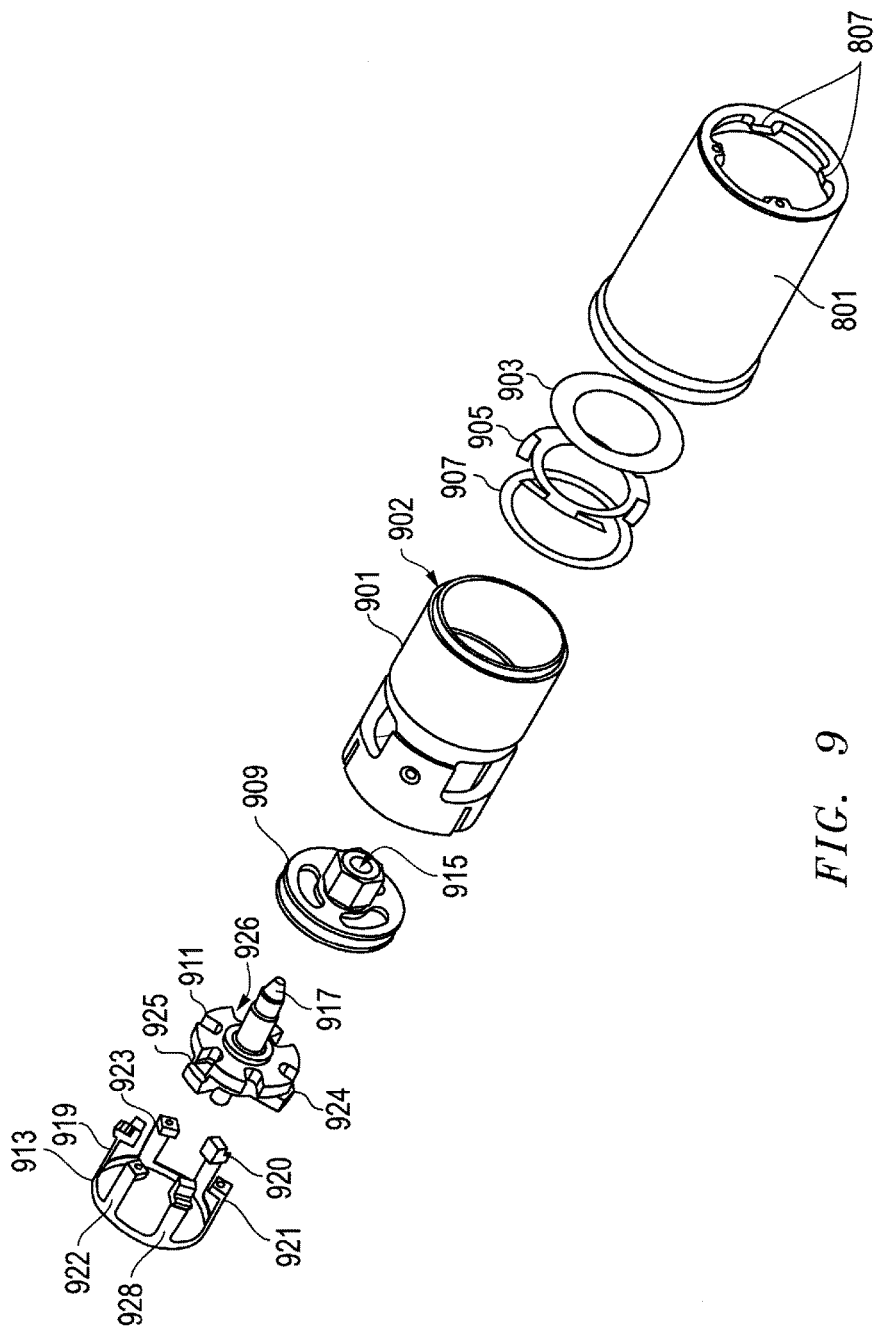
FIG. 9 includes an exploded view of components within a sleeve portion of the surgical tool in accordance with an embodiment.

Referring to FIG. 9, an exploded view of particular components within the sleeve portion of the surgical tool is illustrated in accordance with an embodiment. As illustrated, the outer sleeve portion 801 can include an inner sleeve portion 901 configured to slidably engage within the outer sleeve 801. Additionally, washers 903 and 907 can be disposed on either side of a biasing washer 905 and disposed within the outer sleeve 801. In particular, the washers 903 and 907 and the biasing washer can be disposed at the distal end of the outer sleeve adjacent the flanges 807 and biased against the lip 902 of the inner sleeve 901.

In accordance with a particular embodiment, the surgical tool includes a hex drive gear output 909 selectively coupleable to the motor shaft 911, which in turn is selectively coupleable to a spline driver 913. According to a particular embodiment, the hex drive output gear includes an opening 915 configured to receive the distal end 917 of the motor shaft 911. In accordance with a particular embodiment, the distal end 917 of the motor shaft 911 extends through the opening 915 of the hex drive output gear 909 and is configured to engage the coupling device 613 illustrated in FIG. 6. The spline driver 913 includes splines 918, 919, 920, 921, 922, and 923, (918-923) and in accordance with an embodiment, a portion of the splines 918-923 are configured to couple to portions of the motor shaft 911. In accordance with a particular embodiment, the splines 921, 922, and 923, are configured to fixably attach to portions 924, 925, and 926 of the motor shaft 911. According to another embodiment, the splines 918, 919, and 920, are not fixably coupled to the motor shaft and are flexible portions which can flex radially inside the inner sleeve 901. Such a configuration facilitates selective coupling and decoupling of the motor shaft 911 from the output shaft by axial movement of the outer sleeve 801 and inner sleeve 901 relative to the remainder of the housing.

Figure 10:
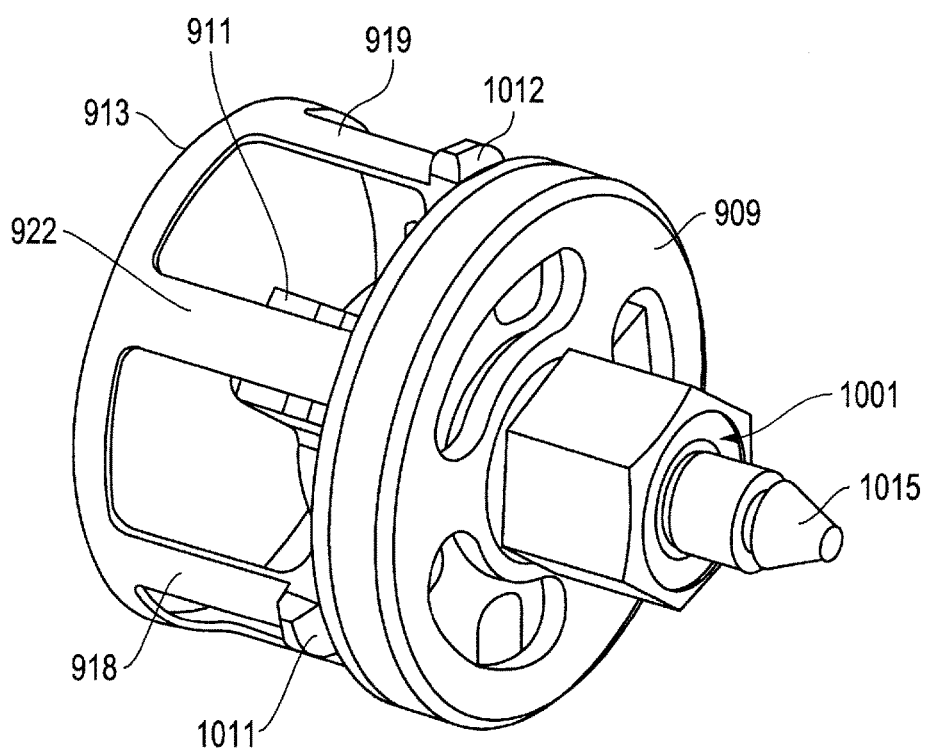
FIG. 10 includes a perspective view of components within the sleeve portion of the surgical tool in accordance with an embodiment.

Referring to FIG. 10, a perspective view of the spline driver, motor shaft, and hex drive output gear are illustrated in accordance with one embodiment. In particular, FIG. 10 illustrates the combination of the hex drive output gear 909 coupled with the motor shaft 911 and further coupled with the spline driver 913. As illustrated, the distal end 1015 of the motor shaft 911 extends through the opening 1001 of the hex drive output gear 909. In accordance with a particular embodiment, the spline driver 913 includes splines 918 and 919 that include portions 1011 and 1012 extending radially outward from the respective splines 918 and 919. The portions 1011 and 1012 are configured to engage a channel within the inner sleeve 901, allowing the splines 918 and 919 to radially expand and clutch portions of the hex drive output gear 909. The coupling of splines 918 and 919 with portions of the hex drive output gear 909 facilitates coupling the motor shaft 911 with the hex drive output gear 909 and as a result coupling the motor shaft 911 with the output shaft.

Figure 11:
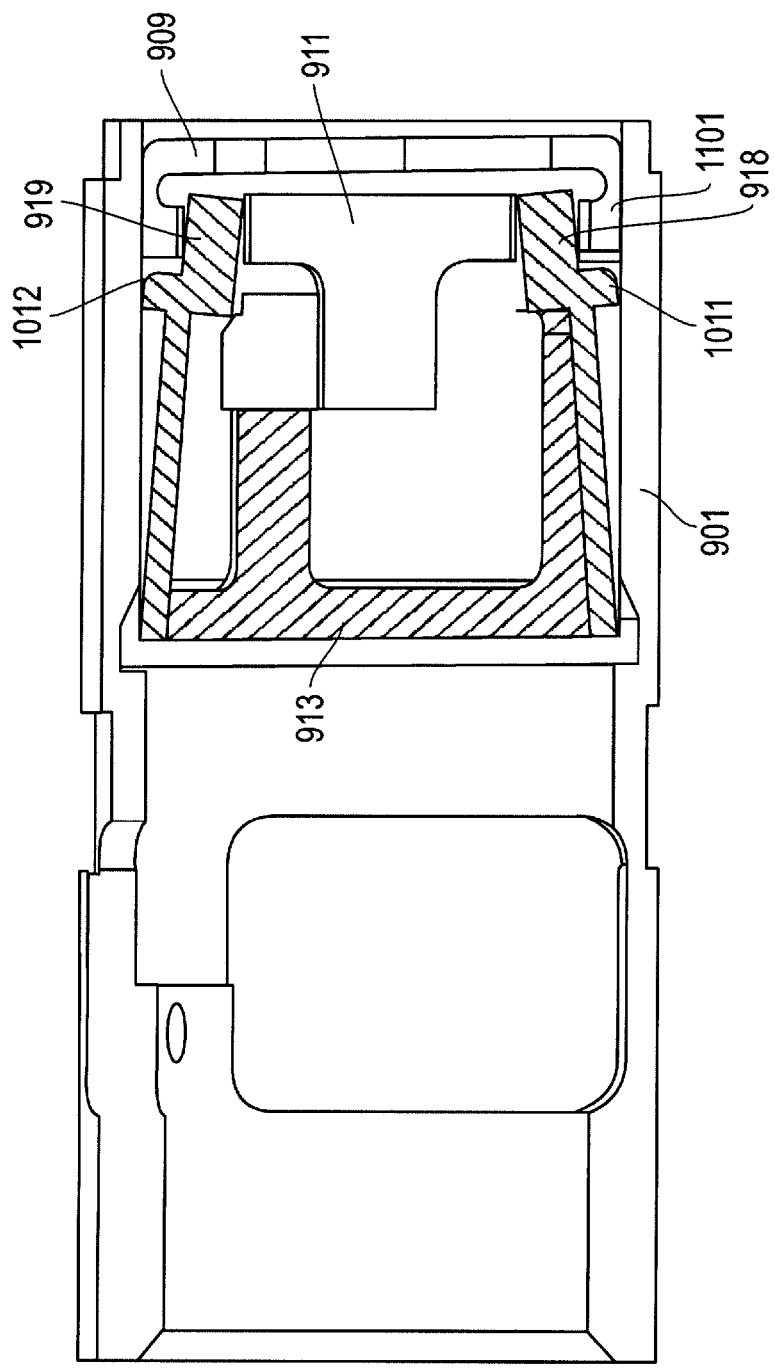
FIG. 11 includes a cross-sectional view of components within the sleeve portion of the surgical tool in accordance with an embodiment.
Figure 12:
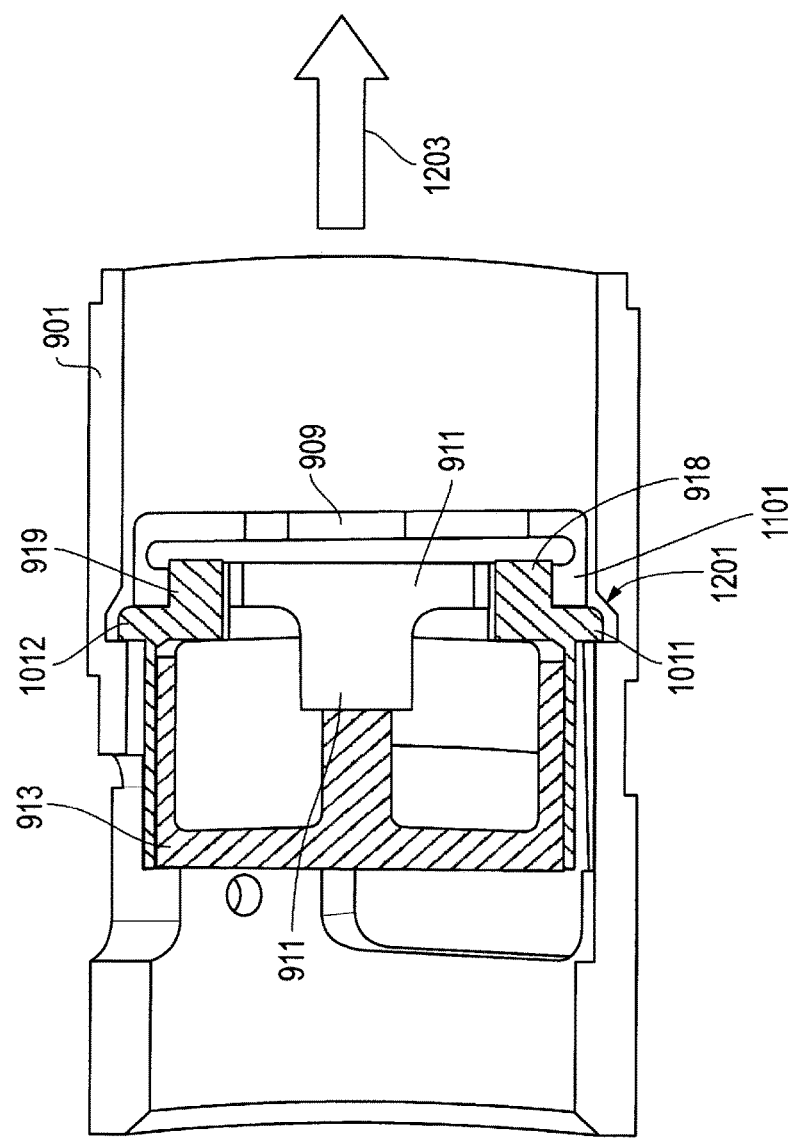
FIG. 12 includes a partial cross-sectional view of components within the sleeve portion of the surgical tool in accordance with an embodiment.

FIGS. 11 and 12 more clearly illustrate the clutching interaction between the spline driver and the hex drive output gear. Referring to FIG. 11, a partial cross-sectional illustration of the spline driver 913, motor shaft 911, and hex drive output gear 909 within the inner sleeve 901 is illustrated. In particular, as illustrated, the spline drive 913 is contained within the inner sleeve portion 901 such that the splines 918 and 919 are radially compressed. According to one particular embodiment, portions 1011 and 1012 engage the side walls of the inner sleeve portion 901 and radially compress the spline portions 918 and 919 thereby decoupling spline portions 918 and 919 from the lip portion 1101 of the hex drive output gear 909.

Referring now to FIG. 12, a partial cross-sectional illustration of portions of components including the spline driver 913, motor shaft 911, and hex drive output gear 909 are illustrated within the inner sleeve portion. Notably, the inner sleeve portion 901 has been moved forward axially in the direction 1203 with respect to the spline driver 913, motor shaft 911, and hex drive output gear 909. Accordingly, in moving the inner sleeve portion 901 forward axially, the splines 918 and 919, and more particularly the portions 1011 and 1012 of the splines 918 and 919 engage a channel 1201 within the inner surface of the inner sleeve portion 901. The engagement of portions 1011 and 1012 within the channel 1201 facilitate outward radial movement of the splines 918 and 919 and coupling of the splines 918 and 919 with the lip portion 1101 of the hex drive output gear 909. The engagement of the splines 918 and 919 with the hex drive output gear 909 facilitates coupling of the motor shaft 911 with the hex drive output gear 909 which in turn facilitates coupling of the motor shaft 911 with the output shaft of the surgical tool. Accordingly, selective coupling and decoupling of the motor shaft 911 with the output shaft is facilitated by axial movement of the inner sleeve portion 901 from a first position to a second position as illustrated in FIGS. 11 and 12 respectively.

Referring briefly again to FIG. 4, coupling of the motor shaft 411 to the output shaft 315 can be accomplished by axial movement of the sleeve portion 307 in the direction 430. In particular, for torque to be applied to the implant, some axial movement of the sleeve portion 307 is completed to couple the motor shaft 411 and the output shaft 315. Such a mechanism ensures that torque cannot be applied to the implant without sufficient engagement of the counter-torque sleeve 313 with the implant, thus avoiding potential for injury to the patient or the surgeon. According to a particular embodiment, the entire allowable movement of the sleeve portion 307, the bayonet portion 309, and the counter-torque sleeve 313 in the axial direction 430 is the axial travel distance 431. In accordance with a particular embodiment, the axial travel distance 431 is generally at least about 10 millimeters, such as at least about 20 millimeters, such as at least about 25 millimeters. In another embodiment, the axial travel distance 431 is limited such that it is not greater than about 50 millimeters, such as not greater than about 40 millimeters. As such, in one particular embodiment, the axial travel distance 431 is within a range between about 15 millimeters and about 30 millimeters.

More particularly, there is a distance 432 that is a fraction of the axial travel distance 431 that is sufficient to selectively couple the splines 918 and 919 within the channel 1201 and thereby couple the motor shaft 411 and output shaft 315. According to one embodiment, the distance 432 is not greater than about 95% of the axial travel distance 431. In another embodiment, the distance 432 is not greater than about 90% or even not greater than about 80% of the axial travel distance 431. Still, in another particular embodiment, the distance 432 sufficient to engage the splines 918 and 919 within the channel 1201 is at least about 50% of the total axial travel distance 431. The differences between the distance 432 and the axial travel distance 431 facilitates partial engagement of the counter-torque sleeve 313 with an implant without requiring the sleeve portion 307 and subsequently the counter-torque sleeve 313 to travel the entire axial travel distance 431 before engagement of the motor shaft 411 with the output shaft 315. Thus, the counter-torque sleeve 313 may not need to extend the entire axial travel distance 431 before the operator can apply rotational force to the implant via the output shaft 315. This may be particularly suitable in the context of performing surgeries where space is limited and full contact with an implant may not be possible.

Figure 13:
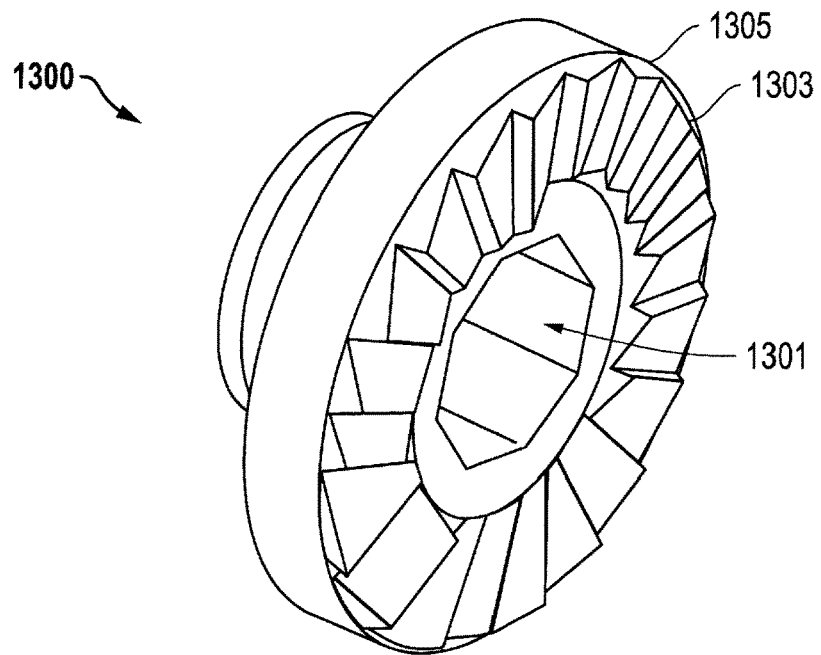
FIGS. 13 and 14 include clutch plates for use in a portion of the surgical tool in accordance with an embodiment.
Figure 14:
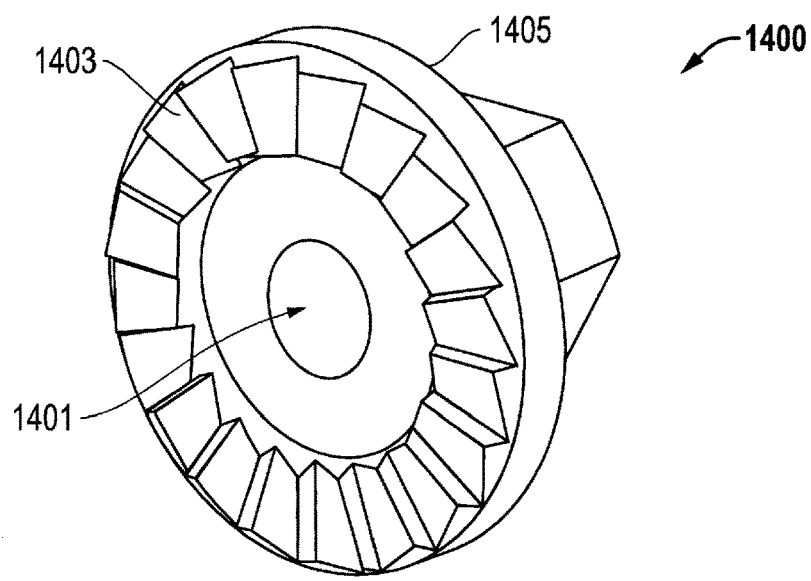

While embodiments herein have demonstrated a selective coupling between the motor shaft and the output shaft using a clutching mechanism having radial splines, it will be appreciated that other mechanisms are possible. For example, turning to FIGS. 13 and 14, alternative clutching mechanisms are illustrated suitable for coupling and decoupling the motor shaft and the output shaft. As illustrated, FIG. 13 includes a face clutch having an opening 1301 configured to couple with a portion of the motor shaft. Additionally, the face clutch includes a series of teeth 1303 disposed along a surface 1305 configured to engage teeth of a corresponding face clutch illustrated in FIG. 14. Accordingly, as illustrated in FIG. 14, the face clutch 1400 includes an opening 1401 configured to engage a portion of the motor shaft, as well as teeth 1403 disposed along the surface 1405 configured to engage the teeth 1303 of the corresponding face clutch 1300. Like the clutching mechanism utilizing the spline driver described previously, the face clutch mechanisms illustrated in FIGS. 13 and 14 are axially displaced until movement of the sleeve portion is sufficient for the faces to engage, wherein the teeth of each surface engage each other and the motor shaft is coupled with the output shaft.

While particular embodiments herein have described mechanical means to selectively couple and decouple the motor shaft from the output shaft, it will be appreciated that electronic devices can be used. For example, in one embodiment, an electronic switch can be used to electrically disengage the motor from the battery until the sleeve portion travels a sufficient distance. As such, according to one embodiment before the sleeve portion is moved in an axial direction, the motor is electrically disengaged from the power source. After movement of the sleeve portion a sufficient axial distance, an electronic switch can be engaged or disengaged such that the motor is electrically coupled to the power source thereby allowing the motor shaft to turn the output shaft. Accordingly, in such embodiments using an electronic device for selective coupling and decoupling, the output shaft and motor shaft may be permanently connected.

Figure 15:
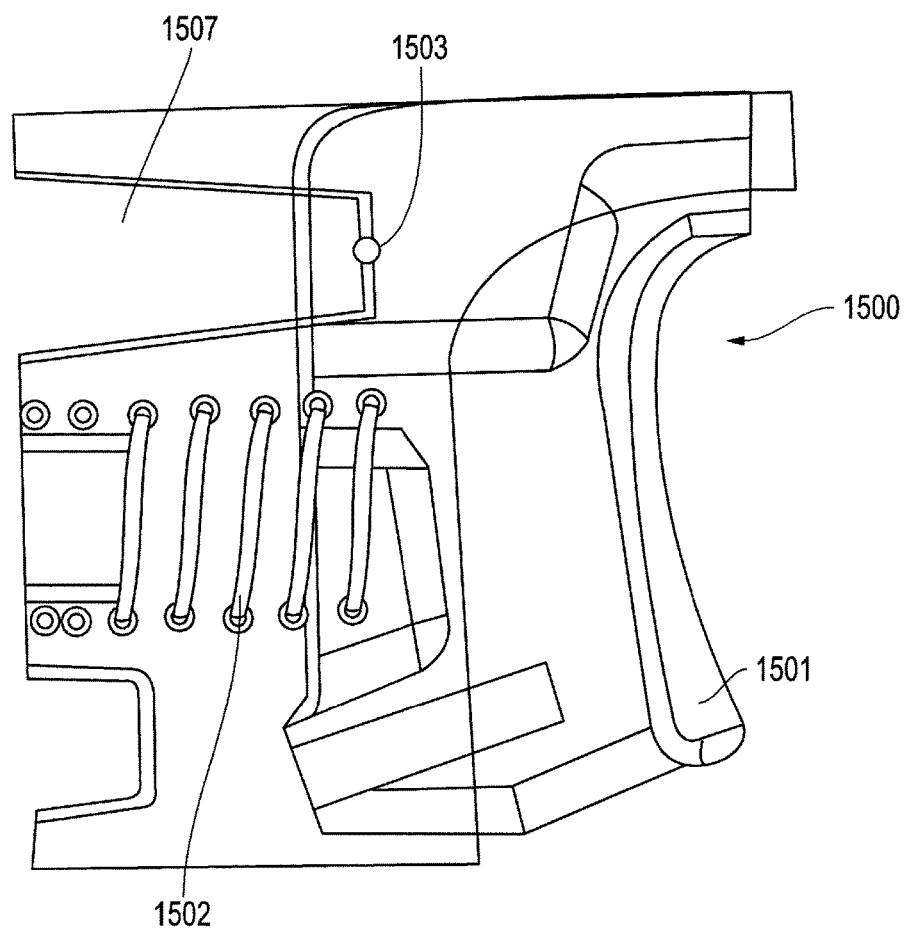
FIG. 15 includes a cross-sectional illustration of a trigger for use with the surgical tool in accordance with an embodiment.

Referring to FIG. 15, a cross-sectional illustration of a trigger in accordance with one embodiment is provided. As illustrated, a trigger 1500 is provided that includes a moveable trigger portion 1501 biased against a base portion 1507 by a biasing member 1502. As illustrated, the moveable trigger portion 1501 and base portion 1507 are pivotally connected at a pivot point 1503, such that the base portion 1507 can be fixably attached to the housing of the handle and the moveable trigger portion 1501 can pivot around the pivot point 1503 upon actuation by a user. In accordance with another embodiment, the trigger 1500 can include a magnetic trigger, including magnetic components, such as a reed switch.

Figure 16:
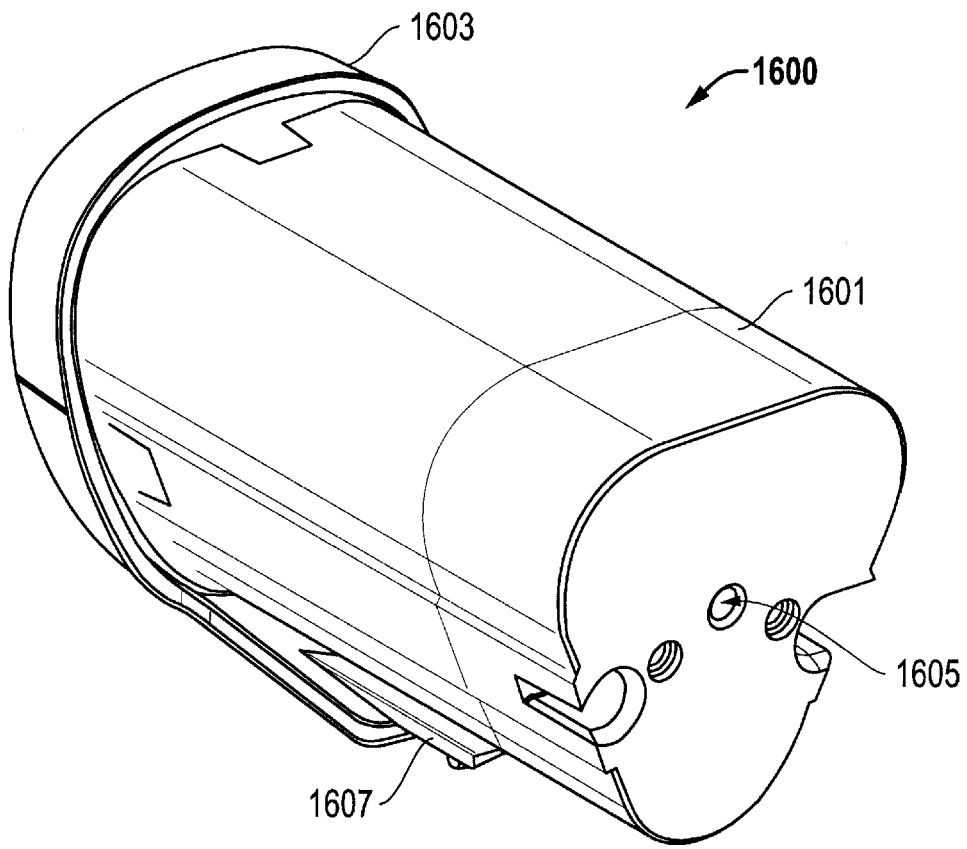
FIG. 16 includes a perspective view of a battery pack for use with the surgical tool in accordance with an embodiment.
Figure 17:
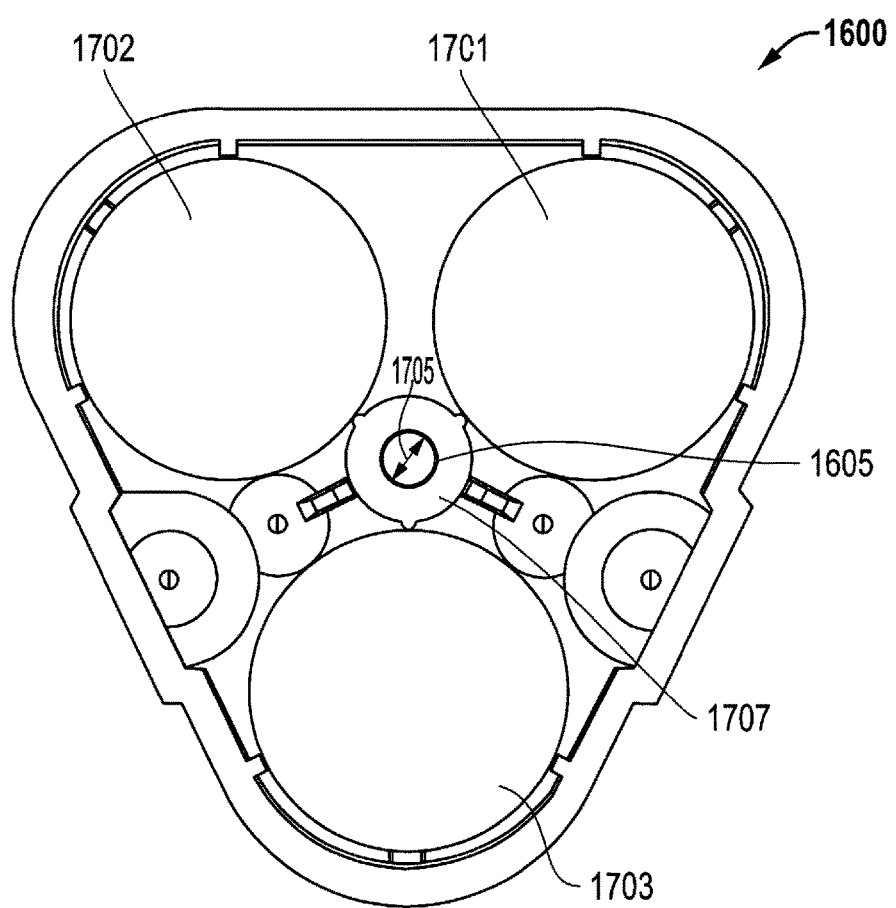
FIG. 17 includes a cross-sectional illustration of the battery pack for use with a surgical tool in accordance with an embodiment.

FIGS. 16 and 17 illustrate particular embodiments of the battery pack. Referring to FIG. 16, a perspective view of a battery pack is illustrated in accordance with one embodiment. As illustrated, the battery pack 1600 includes a housing 1601 for containing the battery or batteries, and a cap portion 1603 coupled at one end of the housing 1601. According to a particular embodiment, the battery pack 1600 further includes a clip 1607 to fixably engage the battery pack 1600 within the housing. Moreover, in accordance with another embodiment, the battery pack 1600 includes a passage 1605 extending through the length of the battery pack 1600.

Referring to FIG. 17, a cross-sectional illustration of a portion of the battery pack is illustrated in accordance with one embodiment. According to one embodiment, the battery pack 1600 has a generally triangular shape having generally three corners, wherein batteries 1701, 1702, and 1703 can be disposed within the three corners of the battery pack 1600. Moreover, in one embodiment, the passage 1605 extends along the longitudinal axis of the battery pack 1600 and between the batteries 1701-1703 such that the batteries 1701-1703 are arranged around the passage 1605. While the embodiment of FIG. 17 illustrated a battery pack 1600 having multiple battery cells 1701-1703, in accordance with another embodiment, the battery pack 1600 can include a single battery cell, such that the interior of the battery pack is one single power cell. In particular, with regard to embodiments using one battery, a passage may still be provided through the battery.

According to one embodiment, the passage 1605 has a diameter 1705 of at least about 1 mm. In another embodiment, the diameter 1705 of the passage 1605 is greater, such as at least about 1.5 mm or at least about 2 mm. In another embodiment, the passage 1605 has a diameter 1705 that is not greater than about 10 mm, such as not greater than about 8 mm, or not greater than about 5 mm. In one particular embodiment, the passage 1605 has a diameter 1705 within a range between 2 mm and about 5 mm.

In accordance with another embodiment, the passage 1605 has an electrically insulating sheath 1707. The electrically insulating sheath 1707 can include a dielectric material. According to one embodiment, suitable dielectric materials can include ceramics or polymers. In a more particular embodiment, the electrically insulating sheath 1707 includes a polymer. In accordance with another embodiment, the electrically insulating sheath can be made of a polymer material, including for example, polyurethane materials, polyolefin materials, polyether materials, silicone materials, or a combination thereof. Further, the polyolefin materials can include polypropylene, polyethylene, halogenated polyolefin, fluoropolyolefin, or a combination thereof. The polyether materials can include polyetherketone (PEK), polyetheretherketone (PEEK), polyetherketoneketone (PEKK), polyaryletherketone (PAEK), or a combination thereof.

Figure 18:
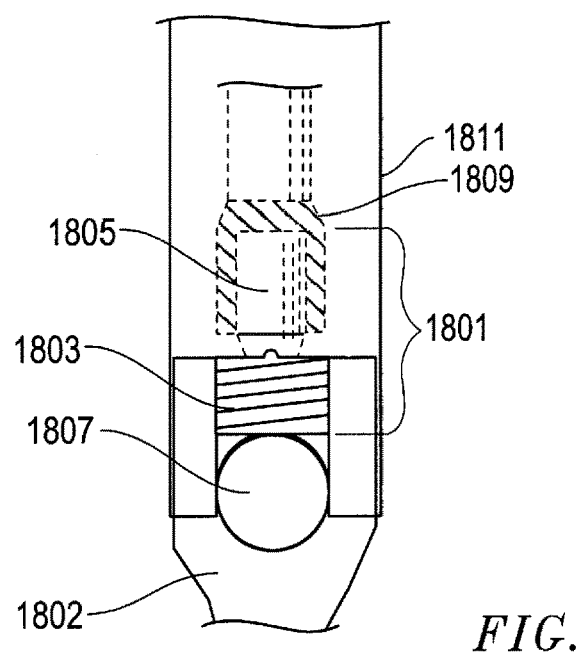
FIGS. 18 and 19 include illustrations of a procedure using the surgical tool to remove a head portion of a set screw in accordance with an embodiment.
Figure 19:
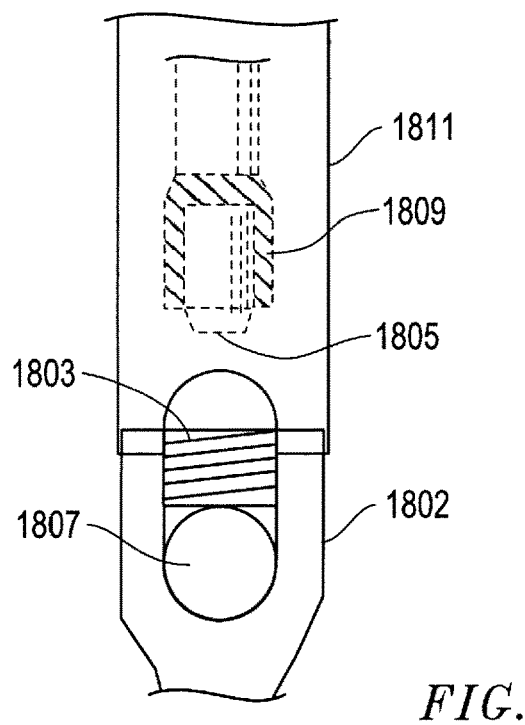

Referring to FIGS. 18 and 19, illustrations are provided that demonstrate the use of the surgical tool for removing a head portion of a set screw. Referring to FIG. 18, a screw 1800 is illustrated that includes a set screw 1801 and a bone screw 1802. The set screw 1801 includes a cap 1803 and a head portion 1805 attached to the cap 1803. The bone screw 1802 includes an opening within a head portion configured to engage a rod 1807 therein and fix the position of the screw 1800 relative to the rod 1807 as is typical with rod and anchor systems. As further illustrated in accordance with one embodiment, the output shaft 1809 is engaged with the head portion 1805 of the set screw 1801 such that it is substantially seated around the head portion 1805. Additionally, the counter-torque sleeve 1811 is configured to extend over the output shaft 1809, the set screw 1801 including the head portion 1805 and the cap 1803, such that the counter-torque sleeve 1811 engages the rod 1807 and the head portion of the bone screw 1802. Notably, the output shaft 1809 and the counter-torque sleeve 1811 engage different portions of the implant.

Accordingly, the output shaft 1809 is configured to provide a rotational force to the head portion 1805, while the counter-torque sleeve 1811 is fixably coupled with the rod 1807 such that it is not free to rotate. The coupling configuration at the implant in conjunction with the output shaft 1809 and the counter-torque sleeve 1811 being coupled at the housing creates a design wherein the rotational forces provided by the output shaft 1809 are balanced by an opposing force of the counter-torque sleeve 1811 at the implant since the two are coupled through the housing.

Referring to FIG. 19 after applying a sufficient rotational force, that is a torsional breaking force to the head portion 1805 via the output shaft 1809 the head portion 1805 can be broken or separated from the cap 1803. Notably during breaking of the head portion 1805 from the cap 1803 the counter-torque sleeve 1811 is fixably engaged with the rod 1807 such that it does not rotate, however rotational forces imparted to the screw by the output shaft 1809 on the head portion 1805 are balanced by the counter-torque sleeve 1811 through the housing. Accordingly, during engagement with the bone screw 1802 and rod 1807, the counter-torque sleeve 1811 is configured to provide a substantially opposite torsional force to the torsional breaking force applied by the output shaft 1809 and substantially fix the position of the bone screw 1802 and rod 1807 relative to the housing of the tool during separating the head portion 1805 from the cap 1803. As such, upon breaking of the head portion 1805 from the cap 1803 the transfer of a sudden release of stored energy to the patient is minimized because of the coupling between the output shaft 1809 and the counter-torque sleeve 1811 with the housing. As a result, jarring of the patient is minimized making the procedure safer and also reducing the likelihood of damage to the implant. Moreover, given the mechanical advantage of using a power tool, the effort expended by the surgeon is substantially less, allowing for a more efficient surgery.

Embodiments provided herein represent a departure from the state of the art. In particular reference to breaking head portions of set screws, the state of the art still includes the use of manual tools often resulting in jarring of the patient and doctor. By contrast, the surgical tool provided herein includes a combination of features making such procedures more efficient and safer. The combination of features include, among other things, use of an output shaft and a counter-torque sleeve coupled to a housing such that the rotational forces generated in the output shaft are balanced in the housing by the counter-torque sleeve. Moreover, other features of the present embodiments include selective coupling and decoupling of the motor shaft with the output shaft, use of a particular axial travel distance, use of electrical power, and certain coupling and clutching mechanisms between the counter-torque sleeve as well as the output shaft thereby facilitating a power tool capable of reducing potential injuries to patients during surgery and making surgeries more efficient and less vigorous on surgeons.

In accordance with a first aspect of the present disclosure a surgical tool for removing a portion of an implant within a human is provided that includes a housing, a motor contained within the housing and coupled to the housing, and an output shaft having a distal end and a proximal end opposite the distal end, wherein the proximal end is coupled to the motor and the distal end has an opening configured to rotatably engage an implant. According to the first aspect, the surgical tool further includes a counter-torque sleeve extending around the output shaft having a proximal end and a distal end opposite the proximal end, wherein the proximal end is coupled to the housing and the distal end configured to couple to the implant relative to the counter-torque sleeve such that upon a rotational force to the implant, the forces transmitted by the output shaft and the counter-torque sleeve are balanced by the coupling of the output shaft and counter-torque sleeve through the housing.

According to one embodiment of the first aspect, the housing comprises an outer sleeve and the counter-torque sleeve is coupled to the outer sleeve. In a particular embodiment, the outer sleeve is slideably engageable with an inner sleeve. In another embodiment of the first aspect, the counter-torque sleeve is slideably engageable over the output shaft. In a more particular embodiment, the counter-torque sleeve is moveable between a first axial position and a second axial position, wherein in the first axial position the output shaft is decoupled from the motor.

In accordance with another embodiment of the first aspect, the implant includes a set screw having a breakable head portion and the output shaft is configured to fit over the head portion. In a particular embodiment, the implant further comprises a rod engaged within a portion of the bone screw and the counter-torque sleeve is configured to engage a portion of the rod.

According to a second aspect of the present disclosure, a tool for use during surgery includes a housing, a motor disposed within the housing and connected to the housing, and an output shaft having a proximal end and a distal end opposite the proximal end, wherein the proximal end is coupled to the motor and the distal end having an opening to engage an implant within a patient. The tool of the second aspect further includes a counter-torque sleeve having a proximal end and a distal end opposite the proximal end, the counter-torque sleeve coupled to the housing and overlying the output shaft, wherein the distal end includes an opening to engage the implant.

According to one embodiment of the second aspect, the output shaft has an opening at the distal end configured to engage an implant. In a particular embodiment, the output shaft has an opening at the distal end configured to fit over a head portion of a set screw. In a more particular embodiment, the opening at the distal end of the counter-torque sleeve is configured to engage a portion of a rod extending through the head portion of the bone screw.

In accordance with another embodiment of the second aspect, the counter-torque sleeve is slideably engageable with the output shaft along a longitudinal axis defined by a length of the counter-torque sleeve over the output shaft. In another alternative embodiment, the distal end of the counter-torque sleeve comprises a conformable head configured to engage an implant. In a more particular alternative embodiment, the conformable head comprises an array of pins, each of the pins in the array moveable between a first axial position and a second axial position to engage an implant.

In one embodiment of the second aspect, the counter-torque sleeve is rotatable around a longitudinal axis defined by a length of the counter-torque sleeve. In another particular embodiment, the counter-torque sleeve is rotatable by not less than about 20°. In a still more particular embodiment, the counter-torque sleeve is rotatable by not greater than about 90°.

According to another embodiment, the tool further includes a viewing port within the counter-torque sleeve and the output shaft. In another embodiment, the tool further includes a torque limiter coupled to the output shaft within the housing. As such, in a more particular embodiment, the torque limiter comprises a microprocessor electrically coupled to the motor.

In accordance with another embodiment of the second aspect, the surgical tool further comprising a battery pack disposed within the housing and having a passage extending through the battery pack. In a more particular embodiment, the battery pack is abutting a proximal end of the housing. In still another particular embodiment, the battery pack comprises multiple power cells. In a still more particular embodiment, the multiple power cells are arranged around the passage. In another embodiment, the battery pack has a longitudinal axis and a substantially triangular cross-sectional contour including three corners, wherein the power cells are disposed within the corners of the battery pack and the passage extends substantially along the longitudinal axis.

In one certain embodiment of the second aspect, the passage has a generally circular cross-sectional contour including a diameter of at least about 1 mm. In a more particular embodiment, the diameter of the passage is not greater than about 10 mm. In accordance with one embodiment of the second aspect, the tool further includes a sealed compartment within the housing. In a particular embodiment, the sealed compartment includes a portion of the housing containing a battery pack and the motor.

In a certain embodiment of the second aspect, the output shaft has a length of at least about 10 cm. In one embodiment, the output shaft has a length of not greater than about 40 cm. In another embodiment, the output shaft has a diameter of at least about 3 mm. In still yet another embodiment, the counter-torque sleeve has a diameter that is greater than the diameter of the output shaft. In another particular embodiment, the counter-torque sleeve has a length of at least about 15 cm. As such, in a more particular embodiment, the counter-torque sleeve has a length of not greater than about 40 cm.

According to a third aspect of the present disclosure a tool for use during surgery includes a housing, a motor disposed within the housing, a battery disposed within the housing and coupled to the motor, and an output shaft having a proximal end and a distal end opposite the proximal end, wherein the proximal end is coupled to the motor. The tool further includes a counter-torque sleeve coupled to the housing having a proximal end and a distal end opposite the proximal end, wherein the counter-torque sleeve is slideably engageable over the output shaft between a first position and a second position, wherein at the first position of the counter-torque sleeve the output shaft is unpowered, and at the second position of the counter-torque sleeve, the output shaft is powered. As such, in one particular embodiment, in the first position of the counter-torque sleeve, the output shaft is decoupled from the motor and thus the output shaft is unpowered. In still another embodiment, at the first position of the counter-torque sleeve, the motor is disengaged from the battery and thus the output shaft is unpowered.

According to one embodiment of the third aspect, the counter-torque sleeve has an axial travel distance and the distance between the first position and the second position is not less than about 50% of the axial travel distance. In another embodiment, the distance between the first position and the second position is not greater than about 90% of the axial travel distance.

In accordance with another embodiment, the tool further includes a trigger moveable between a first position and a second position, wherein at the first position the motor is at an off state and at the second position the motor is at an on state. In a particular embodiment, at the first position of the counter-torque sleeve the motor is at an off state independent of the position of the trigger. In another particular embodiment, the trigger further includes a failsafe switch disposed on the trigger and moveable between an on position and an off position.

In accordance with one embodiment of the third aspect, the tool further includes a trigger coupled to the handle and operable with a first hand of an operator, and a failsafe trigger coupled to the housing, wherein the failsafe trigger is simultaneously operable with the trigger with the first hand of the operator. As such, in another embodiment, the tool further includes a failsafe switch coupled to the housing and moveable between an off position and an on position, wherein the off position is configured to electrically disengage the motor from the battery. In still another embodiment, the tool further includes a failsafe switch coupled to the housing and moveable between an off state and an on state, wherein the off state is configured to disengage the output shaft from the motor.

In another embodiment of the third aspect, the tool further comprising an audible indicator, optical indicator or both coupled to the housing, wherein the audible indicator or optical indicator has a first state corresponding to the first position of the counter-torque sleeve, and a second state corresponding to the second position of the counter-torque sleeve.

According to another aspect of the present disclosure, a tool for use during surgery includes a motor contained within a housing and connected to the housing and an output shaft having a proximal end coupled to the motor and a distal end opposite the proximal end configured to engage a head of a set screw. The tool further includes a counter-torque sleeve coupled to the housing at a proximal end and having a distal end opposite the proximal end configured to fixably engage a portion of an implant adjacent to the head of the screw, and wherein the output shaft is rotated around an axis defined by a length of the output shaft until the head of the screw is separated from a body while the counter-torque sleeve is fixed relative to the implant and head of the screw. In one embodiment, the motor is a DC electric motor.

According to another aspect, a tool for use during surgery includes a motor contained within a housing and connected to the housing, an effector coupled to the motor and configured to provide rotational force to an implant, and a reaction arm coupled to the housing and the implant, the reaction arm configured to react to the rotational force applied to the implant by the effector. In one embodiment, the reaction arm includes a counter-torque sleeve having a proximal end connected to the housing and a distal end configured to engage the implant. In another embodiment, the effector is configured to be coupled to a first portion of an implant and the reaction arm is configured to be coupled to a second portion of the implant, wherein the first portion and the second portion are different portions, and the reaction arm substantially fixes the location of the second portion of the implant relative to the position of the housing. In a particular embodiment, the effector comprises a distal end having an opening configured to engage a set screw, wherein the effector is configured to apply a torsional breaking force to the set screw to separate a head portion of the set screw from a cap portion. In another particular embodiment, the reaction arm is configured to engage a bone screw and rod coupled to the set screw, wherein during engagement with the bone screw and rod, the reaction arm is configured to provide a substantially opposite torsional force to the torsional breaking force applied by the effector and substantially fix the position of the bone screw and rod relative to the housing during separating the head portion from the cap portion.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A surgical tool comprising:
   a housing;
   a motor positioned within the housing;
   a sleeve portion coupled to the housing;
   a spline drive positioned within the sleeve portion;
   a motor shaft coupled to the motor, a proximal end of the motor shaft extending through an opening in the spline drive;
   a hex drive output gear, a distal end of the motor shaft extending through an opening in the hex drive output gear; and
   an output shaft, the sleeve portion being moveable relative to the housing between a first position in which the output shaft is spaced apart from the motor shaft and a second position in which the output shaft engages the motor shaft,
   wherein splines of the spline drive engage a channel within the sleeve portion such that the splines move radially outward and are coupled with a lip portion of the hex drive output gear as the sleeve portion moves from the first position to the second position.

2. A surgical tool as recited in claim 1, wherein the splines include a first spline and a second spline, the first spline comprising a portion that extends radially outward from the first spline, the second spline comprising a portion that extends radially outward from the second spline.

3. A surgical tool as recited in claim 2, wherein the portions of the first and second splines are configured to engage the channel within the sleeve portion to allow the first and second splines to radially expand and clutch portions of the hex drive output gear.

4. A surgical tool as recited in claim 1, wherein the splines are moveable between a first orientation in which the splines are radially compressed and engage side walls of the sleeve portion such that the spline driver is decoupled from the hex drive output gear and a second orientation in which the splines extend radially outward and are coupled with the lip portion such that the spline driver is coupled to the hex drive output gear.

5. A surgical tool as recited in claim 1, wherein the splines are each positioned between second splines of the spline drive, the second splines being fixedly attached to portions of the motor shaft.

6. A surgical tool as recited in claim 1, wherein the splines are each positioned between second splines of the spline drive, the second splines each being positioned in a slot in the motor shaft.

7. A surgical tool as recited in claim 1, wherein the sleeve portion moves between the first and second positions by translating the sleeve portion relative to the housing in opposite directions along an axis defined by the output shaft.

8. A surgical tool as recited in claim 1, further comprising an outer sleeve portion, the sleeve portion being slidably positioned within the sleeve portion.

9. A surgical tool as recited in claim 1, further comprising a battery pack disposed within the housing and having a passage extending through the battery pack.

10. A surgical tool as recited in claim 1, further comprising a counter-torque sleeve coupled to the housing and overlying the output shaft such that the counter-torque sleeve is slideably engageable with the output shaft along a longitudinal axis defined by a length of the counter-torque sleeve over the output shaft.

11. A surgical tool as recited in claim 10, wherein a distal end of the counter-torque sleeve includes an opening, a distal end of the output shaft extending through the opening in the counter-torque sleeve.

12. A surgical tool as recited in claim 10, wherein the counter-torque sleeve and the output shaft are each rotatable about the longitudinal axis.

13. A surgical tool as recited in claim 10, further comprising a bayonet portion coupled to the housing and abutting the counter-torque sleeve.

14. A surgical tool comprising:
   a housing;
   a motor positioned within the housing;
   a sleeve portion coupled to the housing;
   a spline drive positioned within the sleeve portion;
   a motor shaft coupled to the motor, a proximal end of the motor shaft extending through an opening in the spline drive;
   a hex drive output gear, a distal end of the motor shaft extending through an opening in the hex drive output gear,
   wherein the spline drive includes a first spline and a second spline, the first spline comprising a portion that extends radially outward from the first spline, the second spline comprising a portion that extends radially outward from the second spline, the portions of the first and second splines being configured to engage a channel within the sleeve portion to allow the first and second splines to radially expand and clutch portions of the hex drive output gear.

15. A surgical tool as recited in claim 14, further comprising an output shaft, the sleeve portion being moveable relative to the housing between a first position in which the output shaft is spaced apart from the motor shaft and a second position in which the output shaft engages the motor shaft.

16. A surgical tool as recited in claim 14, wherein the splines are moveable between a first orientation in which the splines are radially compressed and engage side walls of the sleeve portion such that the spline driver is decoupled from the hex drive output gear and a second orientation in which the splines extend radially outward and are coupled with the lip portion such that the spline driver is coupled to the hex drive output gear.

17. A surgical tool as recited in claim 14, further comprising a battery pack disposed within the housing and having a passage extending through the battery pack.

18. A surgical tool as recited in claim 14, further comprising:
- a counter-torque sleeve coupled to the housing and overlying the output shaft such that the counter-torque sleeve is slideably engageable with the output shaft along a longitudinal axis defined by a length of the counter-torque sleeve over the output shaft; and
- a bayonet portion coupled to the housing and abutting the counter-torque sleeve.

19. A surgical tool comprising:
- a housing;
- a motor positioned within the housing;
- a sleeve portion coupled to the housing;
- a spline drive positioned within the sleeve portion;
- a motor shaft coupled to the motor, a proximal end of the motor shaft extending through an opening in the spline drive; and
- a hex drive output gear, a distal end of the motor shaft extending through an opening in the hex drive output gear,
- wherein splines of the spline drive are moveable between a first orientation in which the splines are radially compressed and engage side walls of the sleeve portion such that the spline driver is decoupled from the hex drive output gear and a second orientation in which the splines extend radially outward and are coupled with the lip portion such that the spline drive is coupled to the hex drive output gear.

20. A surgical tool as recited in claim 19, further comprising an output shaft, the sleeve portion being moveable relative to the housing between a first position in which the output shaft is spaced apart from the motor shaft and a second position in which the output shaft engages the motor shaft.

* * * * *